United States Patent [19]

Mross et al.

[11] Patent Number: 4,530,910

[45] Date of Patent: Jul. 23, 1985

[54] REGENERATION OF THE $Al_2O_3$ CARRIER MATERIAL OF A SPENT $AG/AL_2O_3$ SUPPORTED CATALYSTS

[75] Inventors: Wolf D. Mross, Frankenthal; Matthias Schwarzmann, Limburgerhof; Juergen Plueckham, Frankenthal; Juergen Dehler, Neuhofen, all of Fed. Rep. of Germany

[73] Assignee: BASF Aktiengesellschaft, Ludwigshafen, Fed. Rep. of Germany

[21] Appl. No.: 543,822

[22] Filed: Oct. 20, 1983

[30] Foreign Application Priority Data

Oct. 28, 1982 [DE] Fed. Rep. of Germany ....... 3239886

[51] Int. Cl.$^3$ .......................... B01J 21/20; B01J 23/96; C07D 301/10
[52] U.S. Cl. ......................... 502/24; 502/25; 502/27; 502/324; 502/341; 502/342; 502/346; 502/348; 502/349; 502/352; 502/503; 549/536; 549/537
[58] Field of Search ..................... 502/24, 25, 27, 348, 502/346, 342, 341, 324, 349, 352, 343, 340, 347, 355, 503, 38, 56; 423/27, 628; 75/118 R

[56] References Cited

U.S. PATENT DOCUMENTS

| | | | |
|---|---|---|---|
| 2,422,172 | 6/1947 | Smith et al. | 502/341 |
| 3,403,111 | 9/1968 | Colgan et al. | 502/355 |
| 3,628,914 | 12/1971 | Gravlier | 423/628 |
| 4,007,135 | 2/1977 | Hayden et al. | 502/340 |

FOREIGN PATENT DOCUMENTS 0046056  2/1982  European Pat. Off. ............. 502/24

Primary Examiner—P. E. Konopka
Attorney, Agent, or Firm—John H. Shurtleff

[57] ABSTRACT

The $Al_2O_3$ carrier material from $Ag/Al_2O_3$ supported catalysts which is obtained after the silver has been removed from such spent catalysts in a conventional manner is regenerated by a method in which the carrier material (a) is treated with an aqueous solution of a water-soluble salt or hydroxide of a metal of group IIA, IIIB or IVB of the Periodic Table or of aluminum, copper, manganese, zinc, cadmium, tin or lead, and the material treated in this manner is then dried, and/or the material (b) is heated at 750–1,500° C. for not less than 10 minutes.

8 Claims, No Drawings

REGENERATION OF THE AL$_2$O$_3$ CARRIER MATERIAL OF A SPENT AG/AL$_2$O$_3$ SUPPORTED CATALYSTS

The present invention relates to the regeneration of the Al$_2$O$_3$ carrier material of Ag/Al$_2$O$_3$ supported catalysts which are used principally for the preparation of ethylene oxide by an addition reaction of oxygen with ethylene.

The present invention also relates to the regenerated carrier material and to the preparation of ethylene oxide using an Ag/Al$_2$O$_3$ supported catalyst whose carrier material has been regenerated by the method according to the invention.

A large number of embodiments of the preparation of ethylene oxide from ethylene and oxygen in the gas phase using a silver catalyst are well known. Also well known are the catalysts used for this purpose, whose active catalytic material essentially consists of silver and whose carrier material is, as a rule, aluminum oxide, generally α-Al$_2$O$_3$, in the form of spheres of 3-10 mm diameter or in another form (eg. cylinders or rings) of similar particle size.

Experience has shown that these catalysts have a life of 2-5 years of operation, after which their activity with regard to both ethylene conversion and ethylene oxide selectivity decreases to such an extent that it is no longer economical to use them.

The active catalytic material, particularly if it contains selectivity-improving dopants, such as alkali metal ions, can be reactivated from time to time by certain washing and subsequent doping processes, but these methods only retard the deactivation of the catalysts and do not prevent it in principle.

Hence, if the catalysts no longer meet the minimum economic requirements, they have to be replaced by fresh catalysts. Hitherto, only the silver was recovered from the spent catalysts, this being done by treatment with nitric acid, and the remaining Al$_2$O$_3$ carrier material was discarded.

There is also the possibility of reusing the relatively expensive carrier material by providing it with a fresh layer of silver; however, it was found that such catalysts are substantially less active, and accordingly have a substantially shorter service life, than those containing fresh Al$_2$O$_3$.

It is an object of the present invention to enable the Al$_2$O$_3$ carrier material from spent Ag/Al$_2$O$_3$ supported catalysts which have been freed from silver to be reused for the preparation of fresh catalysts.

We have found that this object is achieved by a process for the regeneration of the Al$_2$O$_3$ carrier material of Ag/Al$_2$O$_3$ supported catalysts which is obtained after conventional removal of the silver from such spent catalysts, wherein the carrier material (a) is treated with an aqueous solution of a water-soluble salt or hydroxide of a metal of group IIA, IIIB or IvB of the Periodic Table or of aluminum, copper, manganese, zinc, cadmium, tin or lead, and the material treated in this manner is then dried, and/or the material (b) is heated at 750°-1,500° C. for not less than 10 minutes.

The effect of these measures is probably attributable to a neutralization of acid centers which form in the carrier material during treatment with nitric acid, and/or elimination of these centers as a result of water being split off. Furthermore, it is possible that low molecular weight silicas which are capable of migration and are known from experience to have an adverse effect on the activity of the catalyst are converted back to the high molecular weight form incapable of migration.

Among the stated metals, those of group IIA of the Periodic Table, ie. the alkaline earth metals, in particular calcium, have proved to be particularly effective. Aluminum, the earth metals of group IIIB of the Periodic Table, including the lanthanides, and the metals of group IVB of the Periodic Table, ie. titanium, zirconium and hafnium, are also very suitable. For economic reasons, calcium is generally preferred.

The metals can be present as cations, eg. $Cu^{++}$ or $Ca^{++}$, in salts, or as complex cations, eg. $(TiO_2)^{++}$.

Since, as explained above, the acidic centers of the Al$_2$O$_3$ are occupied by the metal cations, and the Al$_2$O$_3$ hence acts as an ion exchanger, the nature of the anions is in principle unimportant, these going into the aqueous solution as acids or water. However, small amounts of these anions remain adsorbed on the Al$_2$O$_3$, and some anions, eg. the halides, sulfate and phosphate, affect the behavior of the catalyst; it is therefore advisable to use those compounds whose anions are known to have no effect, eg. hydroxide, carbonate, nitrate or the anions of carboxylic acids, eg. formate or acetate. The effect of the pretreatment can be demonstrated by a simple test, as can be seen from the Examples, so that the effect of a particular anion can also be readily determined by a preliminary experiment. For economic reasons, the preferred anion is generally hydroxide; where the hydroxides are too sparingly soluble, the nitrate is used.

A low solubility is however sufficient, since it is in any case advantageous to treat the Al$_2$O$_3$ with a dilute aqueous salt solution. Preferred salt concentrations are from 0.01 to 1, in particular from 0.1 to 0.6, % by weight, but higher concentrations, for example as high as 10% by weight, can also be used.

In connection with the assumption that an Al$_2$O$_3$ which has not been after-treated according to the invention is an unsuitable catalyst carrier because it has acidic centers which in turn can be attributed to the process of recovering silver by means of nitric acid, we have observed that the concentration of the treating solution can be lower, the lower the nitric acid concentration used. We have found it particularly useful to remove the silver with about 10% strength by weight nitric acid; accordingly, successful regeneration of the carrier is achieved using a 0.10-0.6% strength by weight salt solution.

A calcium hydroxide solution which is saturated at room temperature (about 0.12% by weight of Ca(OH)$_2$) is a particularly preferred treating solution.

The amount of treating solution is not critical, but for practical reasons about 1-5 liters per liter (bulk volume) of the Al$_2$O$_3$ are used.

The treatment is advantageously carried out at room temperature, and the solution is allowed to act on the carrier material for about 10-300 minutes. Thereafter, the solution is separated off and the Al$_2$O$_3$ is dried in a conventional manner, ie. at about 120°-300° C.

Instead of the treatment with the salt solution in accordance with embodiment (a) of the novel process, the Al$_2$O$_3$ carrier material which has been washed and freed from silver can also be heated at 750°-1,500° C. for about 10-300 minutes in accordance with embodiment (b), the acidic centers presumably being destroyed as a result of the elimination of water, and low molecular weight silicas (which are always present in traces in the alumina material) being converted to higher molecular weight ones.

The two embodiments can of course also be used in combination; which of these methods is preferable in a particular case depends on the operating conditions. Method (b) is simpler, but high-temperature furnaces of adequate size have to be available for this method. In method (a), on the other hand, only small amounts of chemicals are consumed and no special apparatus is required.

If the carrier regenerated according to the invention is then once again coated with silver and, if appropriate, with other conventional additives using one of the large number of conventional methods for this purpose, the resulting catalysts are just as active as those prepared using fresh carrier material.

EXAMPLE 5 kg of a spent Ag/Al$_2$O$_3$ catalyst which had been used for an operating time of 40,000 hours (about 5 years) for the preparation of ethylene oxide and whose activity was no longer economical was freed from silver in a conventional manner with 10% strength by weight nitric acid at room temperature, after which the carrier material was washed three times with completely deionized water.

100 g samples of the carrier were treated with 500 g of an aqueous metal salt solution having a concentration k for one hour at room temperature, and were then dried for 10 minutes at 300° C.

The resulting catalyst carrier materials A'-N' were then provided with an active catalytic material in a conventional manner by impregnating them with a solution of 11.5 g of sec.-butylamine, 3.5 g of water, 13.9 g of silver nitrate and 139 mg of lithium and then drying them in a through-circulation drier at 220° C. These basic catalysts were then impregnated with a solution of 16.1 g of methanol, 400 mg of sec.-butylamine, 200 mg of hydrazine hydrate and 16.4 mg of cesium hydroxide and were once again dried in a through-circulation drier at 200° C.

These ready-prepared activated catalysts A-N contained, in addition to the components of the carrier, 8.0% by weight of silver, 0.015% by weight of lithium and 0.0015% by weight of cesium and corresponded, in respect of their preparation and their composition, to the original catalyst, ie. a well-tried prior art catalyst.

Other catalysts O-R were prepared in a similar manner, but without pretreating the carrier with a salt solution. Instead, the Al$_2$O$_3$ obtained after treatment with nitric acid was heated for t minutes at T°C.

For comparison, two other catalysts X and Y were prepared, using fresh α-Al$_2$O$_3$ as the carrier (X), and using the spent carrier (Y) which had not been subjected to any further treatment.

All catalysts A-R as well as X and Y were comminuted to a particle size of 0.5-0.6 mm diameter, and their activity was tested in a conventional manner in a test reactor containing a catalyst charge of 5 g. To do this, 15 liters/hour of a gas mixture comprising 8% by volume of oxygen, 30% by volume of ethylene, 62% by volume of nitrogen and 1 ppm of vinyl chloride were passed through the catalyst, under 15 bar. The temperature was adjusted so that an oxygen conversion of 50% was achieved in each case. $T_1$ is the temperature after an experimental period of 3 days, and $T_2$ the temperature after an experimental period of 2 weeks. The associated selectivities $S_1$ and $S_2$ indicate the percentage, based on ethylene converted, of ethylene which has reacted to give ethylene oxide.

All experimental data are shown in the Table, which proves that the Al$_2$O$_3$ regenerated in accordance with the invention is equivalent to fresh Al$_2$O$_3$ as a carrier and is superior to untreated material.

TABLE

| Exp. No. | Catalyst treatment | | | | Ethylene oxide preparation | | | |
|---|---|---|---|---|---|---|---|---|
| | Catalyst | Salt | K % by weight | °C. | $T_1$ °C. | $S_1$ % | $T_2$ °C. | $S_2$ % |
| 1 | A | Ca(OH)$_2$ | 0.12 | — | 221 | 81.6 | 221 | 81.7 |
| 2 | B | Ba(OH)$_2$ | 0.75 | — | 223 | 81.1 | 223 | 81.1 |
| 3 | C | Mg(Ac)$_2$ | 0.50 | — | 220 | 81.4 | 220 | 81.6 |
| 4 | D | Zn(Ac)$_2$ | 0.50 | — | 221 | 80.9 | 221 | 80.8 |
| 5 | E | Ca(NO$_3$)$_3$ | 0.90 | — | 220 | 81.1 | 220 | 81.2 |
| 6 | F | Mn(Ac)$_2$ | 0.50 | — | 224 | 80.7 | 225 | 80.6 |
| 7 | G | Al(NO$_3$)$_3$ | 0.75 | — | 219 | 80.6 | 219 | 80.7 |
| 8 | H | Pb(Ac)$_2$ | 0.80 | — | 223 | 80.4 | 224 | 80.4 |
| 9 | I | Ce(NO$_3$)$_3$ | 0.90 | — | 219 | 81.2 | 219 | 81.1 |
| 10 | K | Cu(Ac)$_2$ | 0.50 | — | 232 | 80.0 | 233 | 80.2 |
| 11 | L | (ZrO$_2$)(Ac)$_2$ | 0.90 | — | 218 | 81.3 | 219 | 81.3 |
| 12 | M | Ca(NO$_3$)$_2$ | 0.75 | — | 220 | 81.4 | 220 | 81.5 |
| 13 | N | Ca(HCO$_3$)$_2$ | 0.60 | — | 219 | 81.7 | 219 | 81.6 |
| 14 | O | — | — | 750 | 220 | 81.2 | 223 | 81.0 |
| 15 | P | — | — | 1000 | 221 | 81.5 | 221 | 81.5 |
| 16 | Q | — | — | 1250 | 220 | 81.6 | 220 | 81.5 |
| 17 | R | — | — | 1500 | 219 | 81.4 | 219 | 81.6 |
| V1 | X | — | — | — | 220 | 81.5 | 220 | 81.5 |
| V2 | Y | — | — | — | 228 | 80.9 | 247 | 79.5 |

Ac = Acetate

We claim:

1. A process for the regeneration of the α-Al$_2$O$_3$ carrier material of a spent Ag/Al$_2$O$_3$ supported catalyst which remains after conventional removal of the silver from said spent catalyst, the spent Ag/Al$_2$O$_3$ catalyst being that obtained in the catalytic preparation of ethylene oxide by an addition reaction of oxygen with ethylene in the gas phase, which process comprises:
   (a) treating said remaining carrier material after removal of the silver with an aqueous solution of a water-soluble salt or hydroxide of a metal of group IIA, IIIB or IVB of the Periodic Table or of aluminum, copper, manganese, zinc, cadmium, tin or lead;
   (b) then drying the material as treated in step (a); and
   (c) and coating the dried material with the catalytic silver and an alkali metal dopant.

2. A process as claimed in claim 1 wherein the material treated in step (a) is dried and heated at 750°-1,500° C. for not less than 10 minutes.

3. A process as claimed in claim 1 wherein the material is dried in step (b) at a temperature of about 120°-300° C.

4. A process as claimed in claim 2 wherein the material is dried in step (b) at a temperature of about 120°-300° C. and then heated at 750°-1,500° C. for not less than 10 minutes.

5. A process as claimed in claim 1 wherein the metal of the aqueous treatment solution consists essentially of calcium.

6. A process as claimed in claim 1 using a calcium hydroxide solution in the treatment step (a).

7. A process as claimed in claim 1 wherein the silver has been removed by treatment with a low concentration of nitric acid of not more than about 10% strength, and the carrier is regenerated by treatment in step (a), with a 0.1-0.6% strength by weight salt solution.

8. A process for the regeneration of the α-Al$_2$O$_3$ carrier material of a spent Ag/Al$_2$O$_3$ supported catalyst which remains after conventional removal of the silver from said spent catalyst, the spent Ag/Al$_2$O$_3$ catalyst being that obtained in the catalytic preparation of ethylene oxide by an addition reaction of oxygen with ethylene in the gas phase, which process comprises:
   heating said remaining carrier material after removal of the silver at 750°–1,500° C. for not less than 10 minutes; and
   coating the heated material with the catalytic silver and an alkali metal dopant.

* * * * *

UNITED STATES PATENT AND TRADEMARK OFFICE
CERTIFICATE OF CORRECTION

PATENT NO. : 4,530,910
DATED : July 23, 1985
INVENTOR(S) : Wolf D. Mross, Matthias Schwarzmann, Juergen Plueckhan, and Juergen Dehler It is certified that error appears in the above-identified patent and that said Letters Patent is hereby corrected as shown below:

ON THE FRONT PAGE:

In [54] the title, line 2 after "MATERIAL OF", delete the word "A" so that the title reads:

-- REGENERATION OF THE $AL_2O_3$ CARRIER MATERIAL OF SPENT $AG/AL_2O_3$ SUPPORTED CATALYSTS --.

In [75] Inventors: change the spelling of the third inventor's last name from "Plueckham" to -- Plueckhan --.

Signed and Sealed this

Twenty-second Day of October 1985

[SEAL]

Attest:

DONALD J. QUIGG

Attesting Officer

Commissioner of Patents and Trademarks—Designate